(12) United States Patent
Ploch

(10) Patent No.: US 11,213,629 B2
(45) Date of Patent: *Jan. 4, 2022

(54) SENSOR FOR USE WITH A DRUG DELIVERY DEVICE

(71) Applicant: SANOFI-AVENTIS DEUTSCHLAND GMBH, Frankfurt am Main (DE)

(72) Inventor: Markus Ploch, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/993,913

(22) Filed: Aug. 14, 2020

(65) Prior Publication Data

US 2020/0368440 A1 Nov. 26, 2020

Related U.S. Application Data

(63) Continuation of application No. 16/370,524, filed on Mar. 29, 2019, now Pat. No. 10,773,025, which is a
(Continued)

(30) Foreign Application Priority Data

Jan. 16, 2015 (EP) ..................... 15151370

(51) Int. Cl.
*A61M 5/31* (2006.01)
*A61M 5/315* (2006.01)
(Continued)

(52) U.S. Cl.
CPC ...... *A61M 5/31533* (2013.01); *A61M 5/3155* (2013.01); *A61M 5/3158* (2013.01);
(Continued)

(58) Field of Classification Search
CPC ............ A61M 2205/50; A61M 5/1723; A61M 2205/52; A61M 2205/3306;
(Continued)

(56) References Cited

U.S. PATENT DOCUMENTS 6,221,051 B1 * 4/2001 Hjertman .............. A61M 5/145
604/189
10,245,384 B2 4/2019 Ploch
(Continued)

FOREIGN PATENT DOCUMENTS

CN 1671432 9/2005
CN 102458514 5/2012
(Continued)

OTHER PUBLICATIONS

PCT International Search Report and Written Opinion in International Appln. No. PCT/EP2016/050665, dated May 19, 2016, 13 pages.
(Continued)

*Primary Examiner* — Michael P Stafira
(74) *Attorney, Agent, or Firm* — Fish & Richardson P.C.

(57) ABSTRACT

An optical decoding system including an optical sensor integral with or attachable to a housing of a drug delivery device and configured to be directed at first and second rotatable components of a dose setting and dispensing mechanism of the drug delivery device and a processor configured to: (i) cause the optical sensor to capture images of the first and second rotatable components at least at the beginning and end of a medicament dose dispensing process; (ii) determine a rotational position of both the first and second rotatable components in each of the captured images; and (iii) determine from the rotational positions of the first
(Continued)

and second rotatable components an amount of medicament delivered by the dose setting and dispensing mechanism of the drug delivery device.

22 Claims, 8 Drawing Sheets

Related U.S. Application Data continuation of application No. 15/543,507, filed as application No. PCT/EP2016/050665 on Jan. 14, 2016, now Pat. No. 10,245,384.

(51) Int. Cl.
    *G16H 20/13* (2018.01)
    *G16H 20/17* (2018.01)
    *A61M 5/00* (2006.01)
    *A61M 5/20* (2006.01)
    *A61M 5/24* (2006.01)
    *H04N 5/225* (2006.01)

(52) U.S. Cl.
CPC .... *A61M 5/31551* (2013.01); *A61M 5/31553* (2013.01); *G16H 20/13* (2018.01); *G16H 20/17* (2018.01); *A61M 5/002* (2013.01); *A61M 5/20* (2013.01); *A61M 5/24* (2013.01); *A61M 5/31583* (2013.01); *A61M 2005/3126* (2013.01); *A61M 2205/3306* (2013.01); *A61M 2205/3569* (2013.01); *A61M 2205/3592* (2013.01); *A61M 2205/50* (2013.01); *A61M 2205/502* (2013.01); *A61M 2205/583* (2013.01); *A61M 2205/6063* (2013.01); *A61M 2205/6081* (2013.01); *H04N 5/225* (2013.01)

(58) Field of Classification Search
CPC .... A61M 2205/3569; A61M 2205/502; A61M 5/14244; A61M 2205/3584; A61M 2205/3592; A61M 5/20; A61M 5/1452; A61M 2205/581; A61M 5/14248; A61M 5/172; A61M 2205/8206; A61M 2205/18; A61M 2230/201; A61M 2205/582; A61M 2205/332; A61M 5/16831; A61M 5/1456; A61M 2205/3553; A61M 5/14566; A61M 2205/505; A61M 2205/3331; A61M 2205/3368; A61M 2205/3561; A61M 5/16854; A61M 5/007; A61M 5/142; A61M 2205/6054; A61M 2205/3317; A61M 2005/16863; A61M 5/24; A61M 2205/583; A61M 5/31511; A61M 2205/6072; A61M 5/16827; A61M 2005/14208; A61M 5/5086; A61M 2205/587; A61M 2205/3375; A61M 2205/6018; A61M 5/3129; A61M 5/14546; A61M 5/1413; A61M 5/31525; A61M 2205/14; A61M 2205/60; A61M 5/14276; A61M 5/31568; A61M 2205/6063; A61M 5/3202; A61M 5/16804; A61M 2005/206; A61M 2205/3379; A61M 2207/00; A61M 2005/3126; A61M 5/14216; A61M 2205/3576; A61M 5/002; A61M 2205/70; A61M 2005/14268; A61M 2205/3334; A61M 5/178; A61M 2205/3389; A61M 2205/33; A61M 15/009; A61M 5/145; A61M 15/008; A61M 2005/14264; A61M 2005/3125; A61M 5/00; A61M 35/1785; A61M 5/2033; A61M 2205/12; A61M 15/00; A61M 15/0065; A61M 2005/2013; A61M 2205/6009; A61M 5/30; A61M 2005/1726; A61M 2205/13; A61M 5/1458; A61M 11/00; A61M 2205/3313; A61M 5/1684; A61M 5/16886; A61M 5/315; A61M 2205/3303; A61M 5/1407; A61M 5/326; A61M 2005/14506; A61M 2205/14553; A61M 5/14; A61M 5/1782; A61M 5/44; A61M 15/0083; A61M 5/14526; A61M 2205/17; A61M 2205/584; A61M 5/158; A61M 2205/6081; A61M 2209/086; A61M 15/0068; A61M 35/00; A61M 5/1408; A61M 5/19; A61M 5/2053; A61M 5/365; A61M 5/46; A61M 2005/14252; A61M 2205/3327; A61M 5/3204; A61M 5/31; A61M 2005/2073; A61M 2230/50; A61M 37/00; A61M 5/3157; A61M 5/427; A61M 2005/31518; A61M 2209/06; A61M 5/14236; A61M 2202/0007; A61M 2205/6036; A61M 39/10; A61M 5/16809; A61M 5/1689; A61M 5/31515; A61M 2005/1402; A61M 2005/14296; A61M 2005/14573; A61M 2205/0266; A61M 2205/3523; A61M 2205/702; A61M 2230/63; A61M 5/14228; A61M 5/2448; A61M 16/0808; A61M 2005/14513; A61M 2205/276; A61M 2205/35; A61M 5/168; A61M 5/31553; A61M 15/0091; A61M 2005/1585; A61M 2205/103; A61M 5/1454; A61M 5/16881; A61M 2202/064; A61M 2209/01; A61M 5/3146; A61M 2005/1583; A61M 2205/3104; A61M 2205/3606; A61M 2205/8212; A61M 2230/005; A61M 31/002; A61M 5/31566; A61M 11/007; A61M 11/06; A61M 2205/3365; A61M 2209/045; A61M 5/28; A61M 5/422; A61M 2205/1581; A61M 2209/02; A61M 37/0015; A61M 5/14586; A61M 5/162; A61M 5/16877; A61M 5/31535; A61M 5/31551; A61M 5/31585; A61M 11/02; A61M 16/0463; A61M 16/0833; A61M 5/31533; A61M 5/31556; A61M 15/08; A61M 16/0465; A61M 16/1055; A61M 16/1065; A61M 2005/1426; A61M 2005/314; A61M 2205/43; A61M 2205/58; A61M 39/12; A61M 5/14212; A61M 5/3134; A61M 5/31546; A61M 5/445; A61M 2005/14256; A61M 2210/0618; A61M 39/08; A61M 5/31578; A61M 15/0028; A61M 2005/1403; A61M 2005/3131; A61M 2210/0625; A61M 39/24; A61M 5/16813; A61M 11/042; A61M 15/003; A61M 16/04; A61M 2005/14204; A61M 2039/0267; A61M 2039/0276; A61M 2039/0282; A61M 2039/226; A61M 2039/2426; A61M 21/00; A61M 2202/0216; A61M 2202/0405; A61M 2202/0441; A61M 2202/0445; A61M 2202/0447; A61M 2202/0496; A61M 2202/062; A61M 2202/08; A61M 2205/0503; A61M 2205/106; A61M 2205/32; A61M 2205/3633; A61M 2205/364; A61M 2205/42; A61M 2205/44; A61M
2205/507; A61M 2205/75; A61M
2205/8218; A61M 2205/8287; A61M
2206/22; A61M 2210/0668; A61M
2210/0693; A61M 2210/1025; A61M
2210/1064; A61M 2210/1067; A61M
2210/1071; A61M 2210/1078; A61M
2210/1085; A61M 2230/08; A61M
2230/14; A61M 2230/202; A61M
2230/208; A61M 2230/62; A61M
25/0012; A61M 25/0017; A61M 25/0068;
A61M 25/0069; A61M 25/0071; A61M
25/0147; A61M 25/065; A61M 25/1002;
A61M 25/10184; A61M 25/104; A61M
27/008; A61M 3/00; A61M 3/005; A61M
3/0258; A61M 3/0279; A61M 39/0247;
A61M 5/1422; A61M 5/2066; A61M
5/2455; A61M 5/282; A61M 5/283;
A61M 5/31531; A61M 5/31543; A61M
5/31586; A61M 5/3159; A61M 5/3213;
A61M 5/322; A61M 5/3276; A61M
5/3278; A61M 5/329; A61M 5/3293;
A61M 5/3294; A61M 5/34; A61M 5/344;
A61M 5/345; A61M 5/5013

See application file for complete search history.

(56) References Cited

U.S. PATENT DOCUMENTS

| 10,773,025 | B2 | 9/2020 | Ploch |
| 2006/0224123 | A1 | 10/2006 | Friedli et al. |
| 2014/0194825 | A1 | 7/2014 | Nielsen et al. |
| 2015/0352289 | A1 | 12/2015 | Mercer et al. |
| 2017/0368263 | A1 | 12/2017 | Ploch |
| 2019/0224418 | A1 | 7/2019 | Ploch |

FOREIGN PATENT DOCUMENTS

| CN | 102905613 | | 1/2013 | | |
| CN | 103458940 | | 12/2013 | | |
| CN | 103702699 | | 4/2014 | | |
| EP | 1881859 | B1 * | 1/2011 | ........ | A61M 5/31525 |
| JP | 2014-520584 | | 8/2014 | | |
| WO | WO 2004/009163 | | 1/2004 | | |
| WO | WO-2010098931 A | * | 9/2010 | .......... | A61M 5/3129 |
| WO | WO 2010/142598 | | 12/2010 | | |
| WO | WO 2011/117212 | | 9/2011 | | |
| WO | WO 2012/140052 | | 10/2012 | | |
| WO | WO 2013/004844 | | 1/2013 | | |
| WO | WO-2013004844 A1 | * | 1/2013 | .............. | A61M 5/24 |
| WO | WO-2014023763 A1 | * | 2/2014 | ........ | A61M 5/31525 |
| WO | WO 2014/111340 | | 7/2014 | | |
| WO | WO 2014/111341 | | 7/2014 | | |
| WO | WO 2014/111342 | | 7/2014 | | |
| WO | WO-2014173767 A1 | * | 10/2014 | ............. | G01N 21/55 |

OTHER PUBLICATIONS

PCT International Preliminary Report on Patentability in International Appln. No. PCT/EP2016/050665, dated Jul. 18, 2017, 10 pages.

* cited by examiner

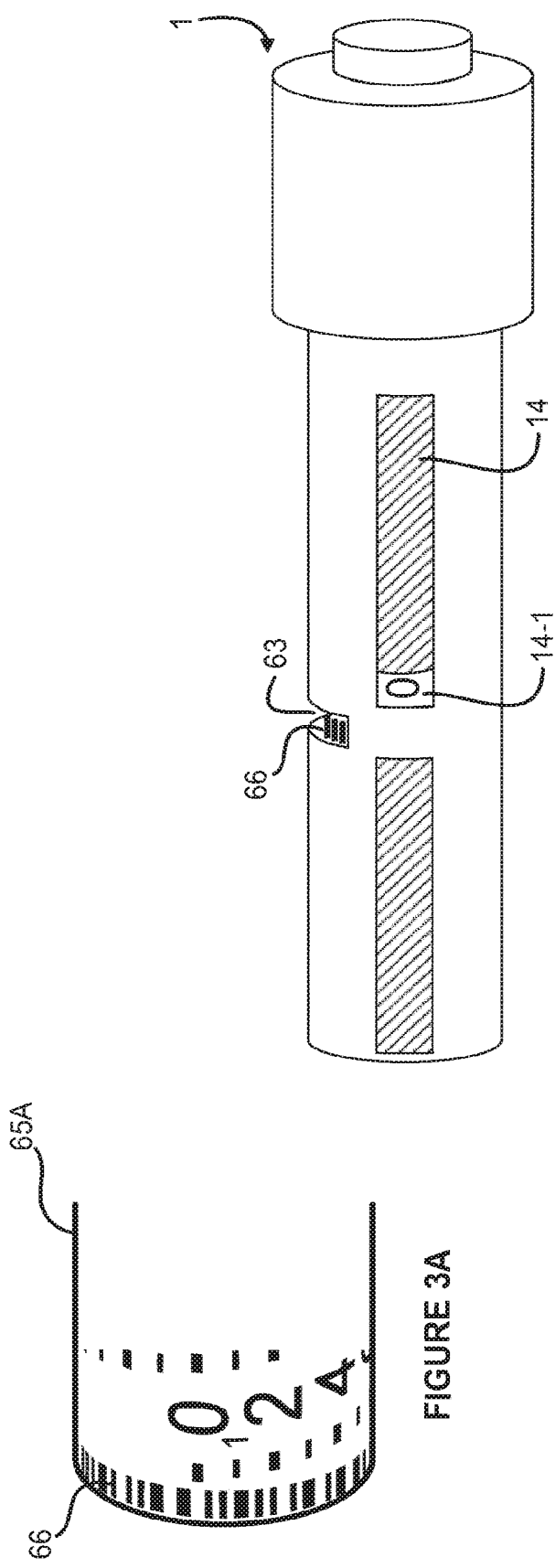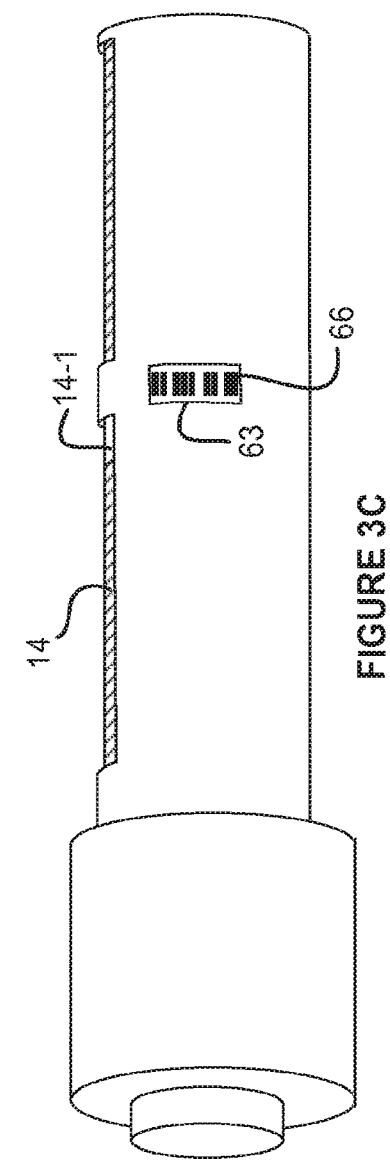

| Number Sleeve | | | Gear Wheel | |
|---|---|---|---|---|
| Rev | Unit | Tooth | Rev | Tooth |
| 1 | 1 | 1 | 1 | 1 |
| 1 | 2 | 2 | 1 | 2 |
| 1 | 3 | 3 | 1 | 3 |
| 1 | 4 | 4 | 1 | 4 |
| 1 | 5 | 5 | 1 | 5 |
| 1 | 6 | 6 | 1 | 6 |
| 1 | 7 | 7 | 1 | 7 |
| 1 | 8 | 8 | 2 | 1 |
| 1 | 9 | 9 | 2 | 2 |
| 1 | 10 | 10 | 2 | 3 |
| 1 | 11 | 11 | 2 | 4 |
| 1 | 12 | 12 | 2 | 5 |
| 1 | 13 | 13 | 2 | 6 |
| 1 | 14 | 14 | 2 | 7 |
| 1 | 15 | 15 | 3 | 1 |
| 1 | 16 | 16 | 3 | 2 |
| 1 | 17 | 17 | 3 | 3 |
| 1 | 18 | 18 | 3 | 4 |
| 1 | 19 | 19 | 3 | 5 |
| 1 | 20 | 20 | 3 | 6 |
| 1 | 21 | 21 | 3 | 7 |
| 1 | 22 | 22 | 4 | 1 |
| 1 | 23 | 23 | 4 | 2 |
| 1 | 24 | 24 | 4 | 3 |
| 2 | 25 | 1 | 4 | 4 |
| 2 | 26 | 2 | 4 | 5 |
| 2 | 27 | 3 | 4 | 6 |
| 2 | 28 | 4 | 4 | 7 |
| 2 | 29 | 5 | 5 | 1 |
| 2 | 30 | 6 | 5 | 2 |
| 2 | 31 | 7 | 5 | 3 |
| 2 | 32 | 8 | 5 | 4 |
| 2 | 33 | 9 | 5 | 5 |
| 2 | 34 | 10 | 5 | 6 |
| 2 | 35 | 11 | 5 | 7 |
| 2 | 36 | 12 | 6 | 1 |
| 2 | 37 | 13 | 6 | 2 |
| 2 | 38 | 14 | 6 | 3 |
| 2 | 39 | 15 | 6 | 4 |
| 2 | 40 | 16 | 6 | 5 |
| 2 | 41 | 17 | 6 | 6 |
| 2 | 42 | 18 | 6 | 7 |

FIGURE 7

SENSOR FOR USE WITH A DRUG DELIVERY DEVICE

CROSS-REFERENCE TO RELATED APPLICATIONS

This application is a continuation of U.S. patent application Ser. No. 16/370,524, filed on Mar. 29, 2019, which is a continuation of U.S. patent application Ser. No. 15/543,507, filed on Jul. 13, 2017, which is a U.S. national stage application under 35 USC § 371 of International Application No. PCT/EP2016/050665, filed on Jan. 14, 2016, which claims priority to European Patent Application No. 15151370.2, filed on Jan. 16, 2015, the entire contents of which are incorporated herein by reference.

TECHNICAL FIELD

The disclosure relates to a sensor assembly which is integrated with or alternatively removably attachable to a drug delivery device such as an injection pen.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning (dialing) a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose.

It has been described, for instance in WO 2011/117212, to provide a supplementary device comprising a mating unit for releasably attaching the device to an injection/drug delivery device. The device includes a camera and is configured to perform optical character recognition (OCR) on captured images visible through a dosage window of the injection pen, thereby to determine a dose of medicament that has been dialed into the injection device.

SUMMARY

A first aspect of the disclosure provides an optical decoding system comprising: an optical sensor integral with or attachable to a housing of a drug delivery device and configured to be directed at first and second rotatable components of a dose setting and dispensing mechanism of the drug delivery device; and a processor configured to: cause the optical sensor to capture images of the first and second rotatable components at least at the beginning and end of a medicament dose dispensing process; determine a rotational position of both the first and second rotatable components in each of the captured images; and determine from the rotational positions of the first and second rotatable components an amount of medicament delivered by the dose setting and dispensing mechanism of the drug delivery device.

The processor may be further configured to cause the optical sensor to capture images of the first and second rotatable components during a medicament dose setting process. The processor may be further configured to determine from the captured images whether the drug delivery device is in a medicament dose dialing mode or a medicament dose dispensing mode. In the medicament dose dialing mode, the first rotatable component may rotate in a first direction and the second rotatable component may remain stationary and in the medicament dose dispensing mode the first rotatable component may rotate in a second direction opposite to the first direction and the second rotatable component may rotate in the first direction.

The processor may be further configured to identify encoded images associated with each of the first and second rotatable components, each encoded image encoding a different rotational orientation of the respective rotatable component.

The lowest common multiple of the number of unique rotational orientations of the first and second rotatable components may be higher than a maximum dose which can be dialed into the drug delivery device. The maximum dose which can be dialed into the drug delivery device may be 120 units.

The processor may be configured to determine the rotational orientation of both the first and second rotatable components at the beginning and end of the medicament dose dispensing process and to use the determined orientations to determine the amount of medicament dispensed.

The first rotatable component may be a hollow cylindrical number sleeve having numbers marked on a first portion of an outer surface. The encoded images may be provided on a second portion of the outer surface. The second rotatable component may be a gear wheel having a plurality of teeth. The encoded images on the gear wheel may be marked on the crests of each gear tooth.

The optical sensor may be configured to be activated by movement of the first rotatable component. The optical decoding system may further comprise a switch. A change in the state of the switch may be configured to cause the optical sensor to be activated.

The drug delivery device and switch may be configured to be arranged such that the state of the switch changes when the drug delivery device moves from a zero unit drug dose arrangement to a single unit drug dose arrangement.

The optical decoding system may further comprise a display device. The processor may be configured to cause the display device to display an indication of the amount of medicament that has been delivered.

The optical decoding system may further comprise one or more LEDs configured to illuminate portions of the first and/or second rotatable components.

The optical decoding system may be part of a supplementary device configured to be attached to the drug delivery device.

A second aspect of the disclosure provides a medicament delivery system comprising:

a drug delivery device comprising first and second rotatable components each having a plurality of encoded images disposed around an outer surface thereof, and wherein each of the encoded images corresponds to a discreet rotational orientation of the respective component; and an optical decoding system according to any preceding claim retained in a housing of the drug delivery device.

In the medicament delivery system: the first rotatable component may be a hollow cylindrical number sleeve having numbers marked on a first portion of an outer surface; the encoded images on the number sleeve may be provided on a second portion of the outer surface; the second rotatable component may be a gear wheel having a plurality of teeth; and the gear wheel may be engaged with a drive sleeve of the drug delivery device during the medicament dose dispensing process.

The number of encoded images on the number sleeve may be 24 and number of encoded images on the gear wheel may be 7.

BRIEF DESCRIPTION OF THE DRAWINGS

For a more complete understanding of example embodiments of the present disclosure, reference is now made to the following description taken in connection with the following Figures, in which:

FIGS. 3A to 3C are illustrative simplified views of various components of a drug delivery device with which sensor devices according to various embodiments of the disclosure may be used;

FIG. 7 is a table illustrating the rotational orientations of the rotatable components of the drug delivery device at different medicament doses.

DETAILED DESCRIPTION

Figure 1:
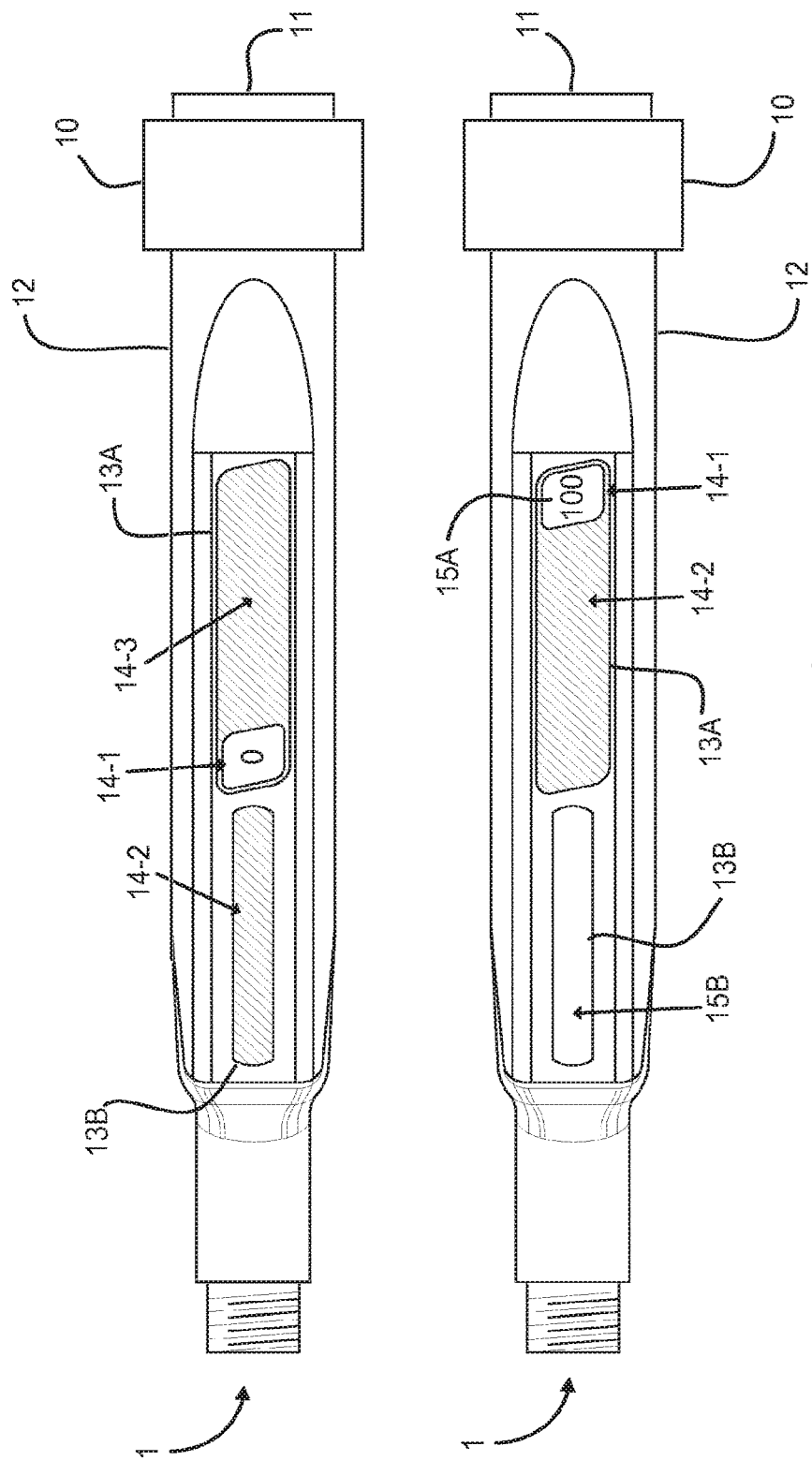
FIG. 1 shows two views of a drug delivery device 1 with which a sensor device according to various embodiments of the disclosure may be used.

The drug delivery device 1 of FIG. 1 is configured such that a user is able to adjust the drug dosage (or number of drug doses) that is to be delivered (or dispensed) using the device 1. In the example of FIG. 1, this is achieved by rotating (or dialing) a dose selector 10 which causes an internal dialing mechanism (not shown) to adjust an amount of the drug that is to be dispensed once a drug delivery mechanism (not shown) is actuated. In this example, the drug delivery mechanism is actuated by pressing a button 11 on the device.

The drug delivery device 1 comprises an external housing 12 in which is formed at least one aperture or window 13A, 13B. As will be appreciated, an aperture may simply be a cut-away area of the external housing 12, whereas a window may be a transparent portion of the housing through which components of the device may be seen. For convenience, the at least one aperture or window 13A, 13B, will hereafter simply be referred to as the at least one window.

The at least one window 13A, 13B allows a movable gauge element 14 to be visible from the exterior of the housing 12. The drug delivery device is configured such that as the dose selector 10 is dialed, the movable gauge element 14 is caused to be moved thereby to indicate a selected dose to the user. More specifically, as the dose selector 10 is dialed, the gauge element 14 moves axially along an underlying surface 15A, 15B thereby to indicate the selected dose. In the example of FIG. 1, a surface 15A underlying at least part of the gauge element 14 comprises a number sleeve 15A. The number sleeve 15A has numbers indicative of drug doses provided on its outer surface, with the number indicating the currently selected dose being visible through the at least one window 13A, 13B. In this example, the number sleeve 15A is visible through a gauge window (or aperture) 14-1 formed in the movable gauge element. Other parts of the movable gauge element 14 are discussed below.

The uppermost view of the drug delivery device 1 shown in FIG. 1 illustrates the situation before any dialing has been performed. Consequently, the movable gauge element 14 is at its first (or initial) position at a first end of the path along which it is able to move. In this example, when the movable gauge element 14 is at the first end of its path, the portion of the number sleeve 15A that is visible through the gauge window 14-1 shows the number zero (i.e. a zero dose).

The bottommost view of the drug delivery device 1 shown in FIG. 1 illustrates the situation after dialing has been performed. Consequently, the movable gauge element 14 has moved axially along the path that is visible through the first window 13A away from its first position. In this example, the device 1 has been dialed to its maximum dose and as such, the movable gauge element 14 has moved to the second end of its path. The maximum dose in this example is "100" and so the portion of the number sleeve 15A that is visible through the gauge window 14-1 shows the number "100". In some other embodiments, the maximum dose is "120", however the amount of medicament or individual doses able to be dialed into the device is not essential.

In this example, the device 1 comprises first and second windows 13A, 13B. The number sleeve 15A underlies and is visible through the first window 13A, whereas a further underlying element 15B underlies and is sometimes visible through the second window 13B. The further underlying element 15B may or may not include any numbers. The further underlying surface 15B is visually distinguishable from a second part 14-2 of the movable gauge element 14 which overlies it and which is configured to move axially along it. For instance, the second part 14-2 of the movable gauge element 14 may be of a different reflectance to the further underlying surface 15B. For example, one of the gauge element 14 and the underlying surface 15B may be of a light color (e.g. may be made of a light colored polymer) and the other may be of dark color (e.g. may be made of a dark colored polymer). The user may, therefore, be able to determine the selected dose by determining the proportion of the second window 13A in which the gauge element 14 (specifically, the second part 14-2) is visible compared to the proportion in which the further underlying surface 15B is visible. This can be seen from FIG. 1, in which, when the device 1 is dialed to its zero dose, the gauge element 14 covers the entire length of the path that is visible through the second window 13B. In contrast, when the device 1 is dialed to its maximum dose, none of the gauge element 14 is visible through the second window. Instead, the further underlying surface 15B is visible along the entire length of the path defined by the second window 13B.

The number sleeve 15A (which is also the surface underlying the gauge element 14) is also visually distinguishable from the movable gauge element 14 which overlies it and which is configured to move axially along it. For instance, gauge element 14 may be of a different reflectance to the number sleeve 15A. For example, one of the gauge element 14 and the underlying surface 15A may be of a light color (e.g. may be made of a light colored polymer) and the other may be of dark color (e.g. may be made of a dark colored polymer). In the examples shown in the Figures, the number sleeve 15A and underlying surface 15B are of a higher reflectance than the movable gauge element 14.

FIGS. 2A to 2E are simplified schematics of components of a drug delivery device such as that of FIG. 1. The purpose of FIGS. 2A to 2E is to illustrate the operation of a drug delivery device 1 such as that of FIG. 1; they are not intended to be accurate representations of the exact design of the components.

Figure 2A:
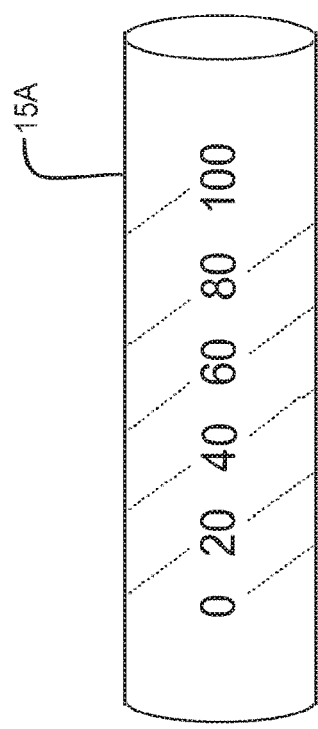
FIGS. 2A to 2E are illustrative simplified views of various components, and combinations of components, of a drug delivery device such as that of FIG. 1 with which a sensor device according to various embodiments may be used.

FIG. 2A is a simplified schematic of the number sleeve 15A. The sleeve 15A has numbers provided on its surface. In some examples, the numbers, ranging from the minimum dose to the maximum dose, may be provided helically around the surface of the number sleeve.

Figure 2B:
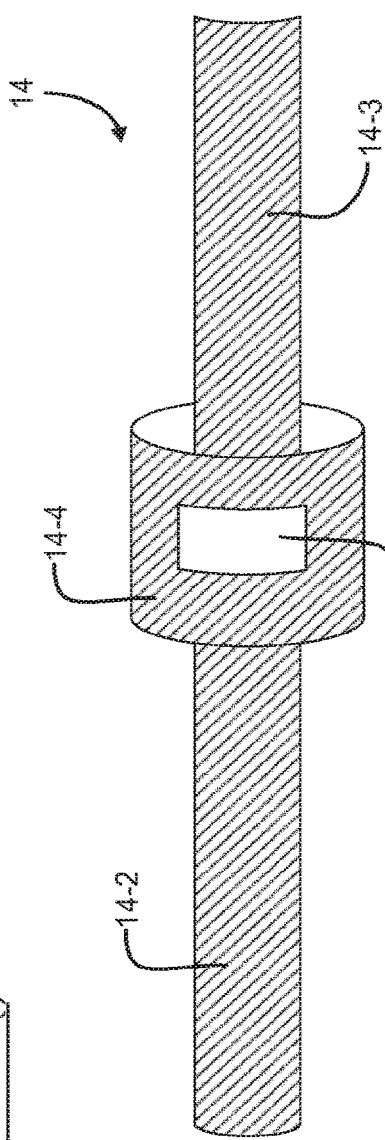
Figure 2C:
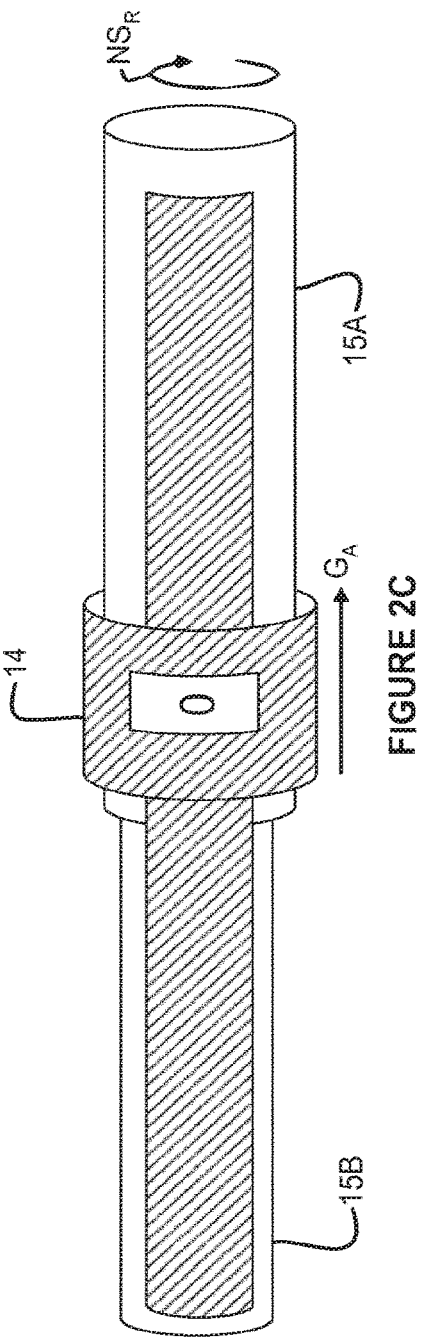
Figure 2D:
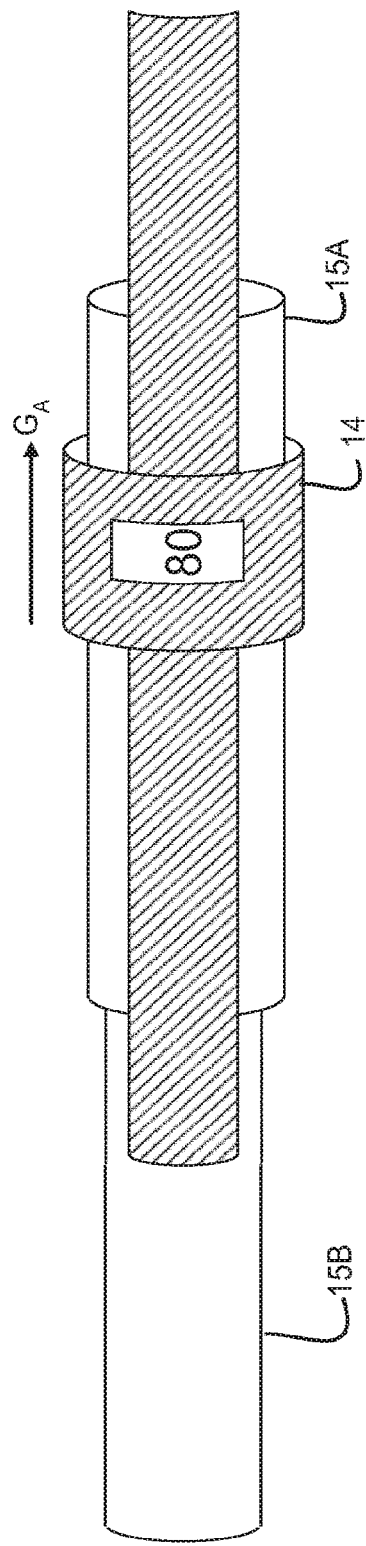

FIG. 2B is a simplified schematic of a movable gauge element 14. The gauge element 14 comprises a first section 14-4 in which the gauge window 14-1 is provided. In this example, the first section is 14-1 a collar which is configured to encircle the number sleeve 15A (as can be seen in FIGS. 2C and 2D). Extending in opposite directions from the first section 14-4 are the second part 14-2 and a third part 14-2. The second and third parts 14-2, 14-3 extend generally parallel to the longitudinal axis of the number sleeve.

The second part 14-2 of the movable gauge element is configured to extend from the first part 14-2 by a length sufficient to fill the entire second window 13B when the movable gauge is in its first position. The second part 14-2 may also serve to obscure a portion of the exterior surface of the number sleeve 15A, when the gauge element moves away from its first position. The third part of the movable gauge element 15-3 is configured to obscure a portion of the exterior surface of the number sleeve 15A, when the gauge elements moves between its first and second positions. In this way, only the portion of the number sleeve that underlies the gauge window 14-1 is visible through the first window 13A of the device housing 12.

The number sleeve 15A is rotatable about its longitudinal axis within the device housing 12. As such, the number sleeve 15A may be referred to as a movable (or rotatable) component. Rotation of the number sleeve 15A is in some embodiments caused by rotation of the dose selector 10.

The rotational movement $NS_R$ of the number sleeve 15A and axial movement $G_E$ of the gauge element 14 are interdependent. Put another way, the dialing mechanism of the device 1 is configured such that when number sleeve 15A is caused to rotate, the gauge element 14 is caused to move or translate axially along its path. Moreover, the degree of rotation of the number sleeve 15A corresponds proportionally to the extent of axial movement of the gauge element 14.

Figure 2E:
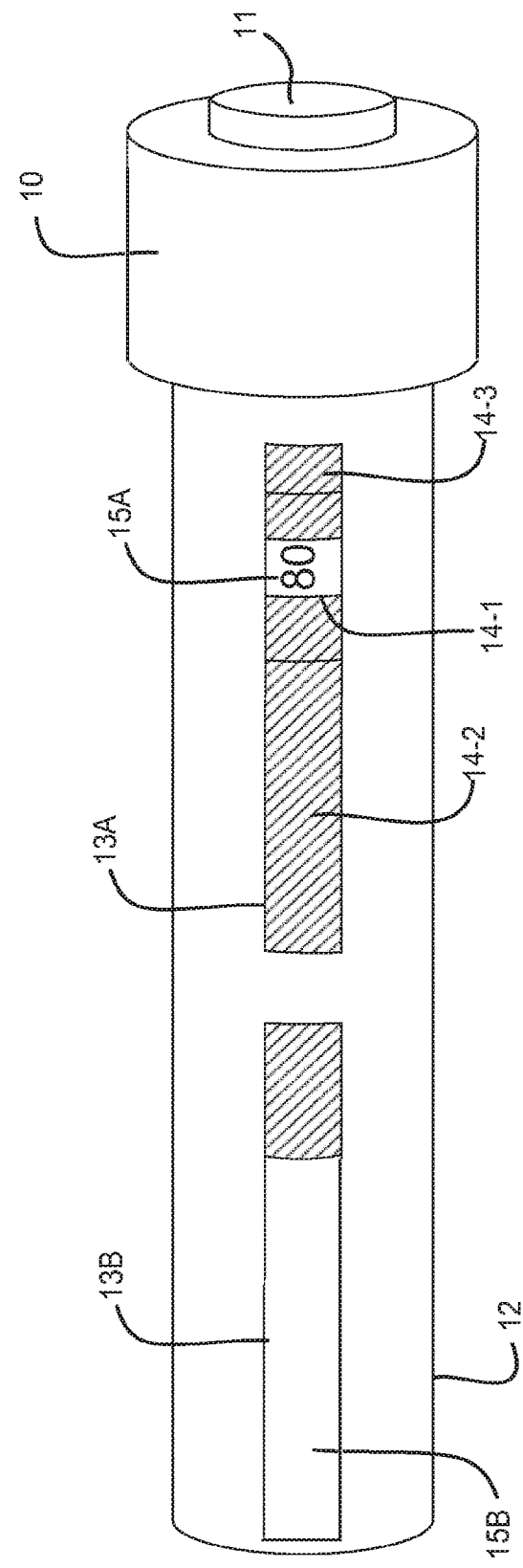

FIG. 2C shows the gauge element 14 in its initial position in which, in this example, it indicates a zero dose. FIG. 2D shows the number sleeve 15A and gauge element 14 following rotation of the number sleeve 15A and translation of the gauge element 14 from its first position. FIG. 2E shows this arrangement of FIG. 2D within a simplified version of the device housing 12.

FIG. 3A shows an example of a rotatable component 65A, in this instance a number sleeve 65A, which may form part of a drug delivery device 6 for use with sensor devices 2 according to embodiments of the disclosure. FIGS. 3B and 3C show two different simplified views of a delivery device 6 including the rotatable element 65A of FIG. 3A. The delivery device of FIGS. 3A-C may be generally the same as that described with reference to the previous figures except for the differences described below.

As with the previously described delivery device 1, the rotation of the rotatable component 65A is interdependent with the axial movement of the movable gauge element 14. The degree of rotation may be proportional to the axial movement of the movable gauge element 14. In the examples of FIG. 3A, the rotatable element 65A has, provided around its exterior surface, a visually-distinguishable code 66 for allowing its rotational orientation to be determined. For example, the mechanism of the delivery device 1 may be arranged so that one full rotation of the number sleeve 15A corresponds to 24 dialed units of medicament. Thus the number sleeve 15A may be rotatable into any one of 24 unique rotational orientations. For each of these rotational positions a different code may be provided. The code 66 may take any suitable form so long as it allows the rotational orientation of rotatable element to be determined by the sensor device 2. In this example, the code 66 is provided at an end of the number sleeve 65A.

The housing 12 of the drug delivery device 6 includes a further aperture or window 63 through which a portion of the rotatable element 65A, on which part of the code 66 is provided, is visible. The further window 63 is positioned and oriented relative to the rotatable element 65A such that a portion of the code is externally visible through the further window 63 regardless of the rotational orientation of the rotatable element 65A. The further window 63 is positioned and oriented relative to the rotatable element 65A such that, as the rotatable element rotates through a single complete rotation, a different section of the code 66 is visible at each rotational orientation. The further aperture is, in this example, provided on a different side of the device housing 12 (or, if the housing is cylindrical or otherwise rounded, around the exterior surface of the device housing 12) from the at least one window 13A, 13B through which the movable gauge element 14 is visible. In this way, the movable gauge element 14 does not obstruct the code from view.

Figure 4:
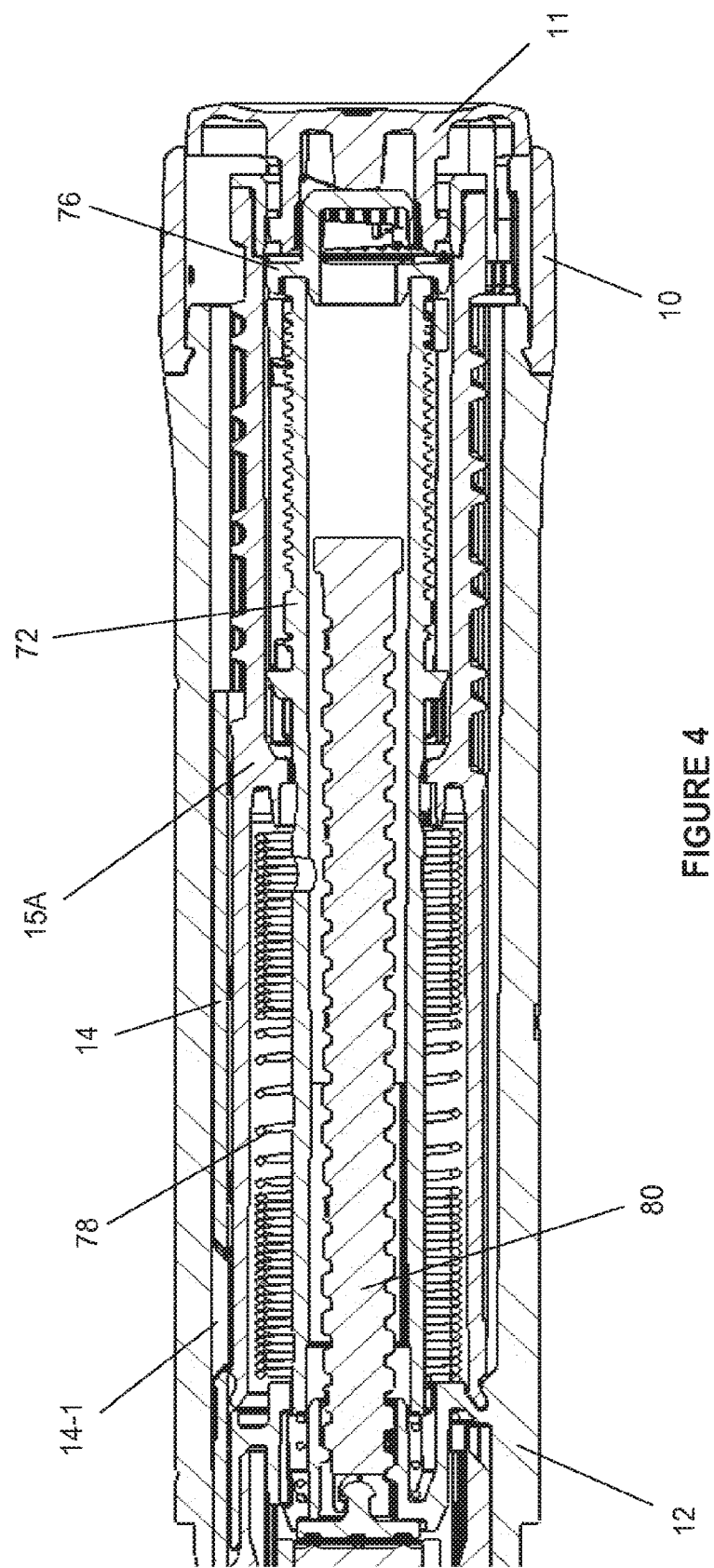
FIG. 4 is a cross-section showing a drug dose setting and dispensing mechanism of a drug delivery device.

FIG. 4 shows a cross-sectional view of a medicament setting and delivery mechanism of a drug delivery device 1. The further window 63 is not shown in FIG. 4. As previously described, the drug delivery device 1 has two modes of operation, a medicament dose dialing mode and a medicament dose delivery (or dispensing) mode. The medicament setting and delivery mechanism comprises a drive sleeve 72, which is a hollow cylindrical component. The drive sleeve 72 is arranged so that it does not rotate during dialing. A torsion spring 78 is provided which is secured at one end to the body of the drug delivery device 1 and at the other end to the number sleeve 15A. The torsion spring 78 biases the number sleeve 15A towards the zero dose position. When the number sleeve 15A is rotated to dial in a dose, the tension in the torsion spring 78 is further increased. The drive sleeve 72 may have a splined interface with an inner part of the body of the drug delivery device 1 which prevents relative rotation during dose dialing. The drive sleeve 72 is also in contact with a clutch member 76 connected to the button 11. When the delivery button 11 is depressed the drive sleeve 72 is therefore moved longitudinally. This moves the splines on the drive sleeve 72 out of engagement with the splines on the body so that the drive sleeve is free to rotate. Further splines on the drive sleeve 72 engage with corresponding splines on the number sleeve 15A when the button 11 is depressed so that rotation of the number sleeve 15A under action of the torsion spring also causes rotation of the drive sleeve 72.

A lead screw 80 is provided in the body of the drug delivery device 1. Axial advancement of the lead screw 80 causes medicament to be expelled from the medicament cartridge. The lead screw 80 is rotationally locked relative to the drive sleeve 72 via a splined interface and has a threaded connection to the body of the drug delivery device 1. Therefore, when the drive sleeve 72 rotates during a medicament dispensing process, the lead screw 80 also rotates and is forced to advance axially by the threaded connection to the body.

Figure 5A:
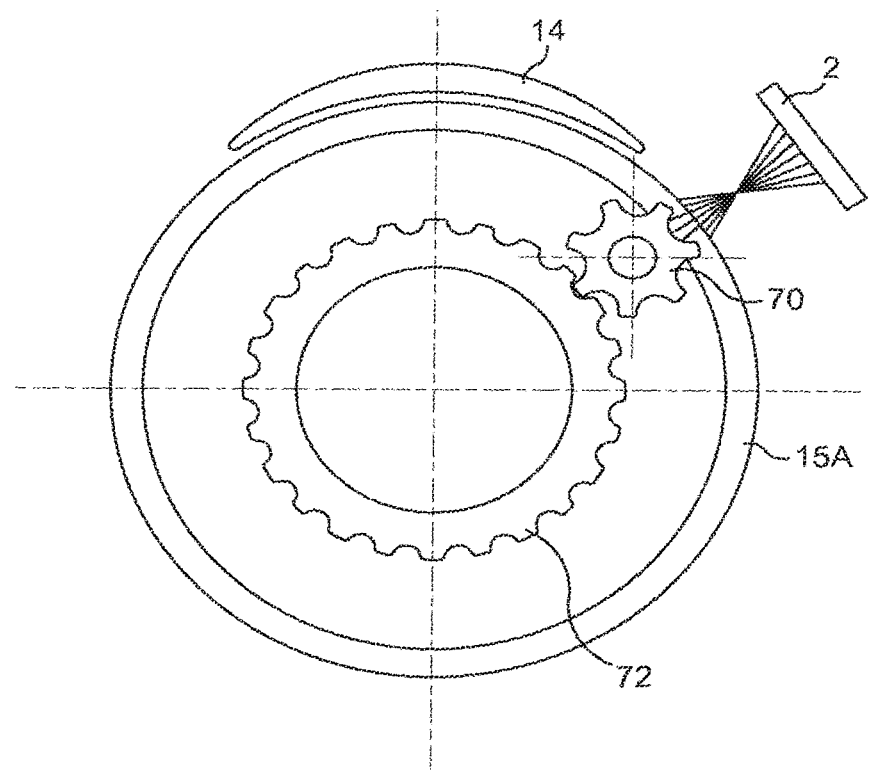
FIG. 5A is a cross-section showing some components of a drug dose setting and dispensing mechanism of a drug delivery device for use in the present disclosure and a schematic illustration of an optical sensor arrangement according to embodiments of the disclosure.

In embodiments of the disclosure, the drug delivery device 1 comprises an additional gear wheel 70 which is not shown in FIG. 4, but is visible in FIG. 5A. The gear wheel 70 is rotatably mounted in the housing and is visible through the further window 63. The gear wheel 70 may be mounted on a pin, or may have an integrally molded axle which is retained in a recess provided in the housing. In some embodiments, the gear wheel is a toothed gear which can engage with corresponding teeth provided on the cartridge end of the drive sleeve 72.

Figure 5B:
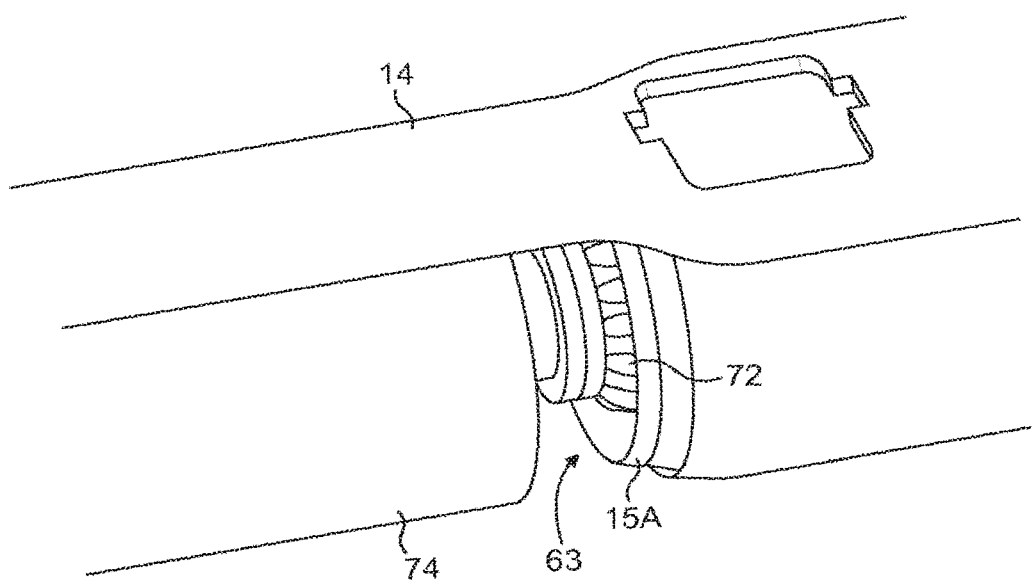
FIG. 5B is a perspective view showing some components of a drug dose setting and dispensing mechanism of a drug delivery device for use in the present disclosure.

The drive sleeve 72 is visible in cross-section in FIG. 5A. The end of the drive sleeve 72 showing the teeth on the outer surface is visible in perspective in FIG. 5B. The medicament cartridge holder 74 is also visible in FIG. 5B.

The drug delivery device may include an optical sensor arrangement 2, shown schematically in FIG. 5A. The optical sensor arrangement 2 may in some embodiments be part of a supplemental device designed to be releasably attachable to the drug delivery device 1. In some other embodiments, the optical sensor arrangement 2 is an integral part of the drug delivery device 1. The optical sensor arrangement 2 is arranged and has a field of view such that it can capture images of the gear wheel 70 and portion of the number sleeve 15A containing the visually-distinguishable code 66. The optical sensor arrangement 2 may capture a single image in which both of these components are visible, or may capture images of each component separately in quick succession.

The gear wheel 70 has a number of encoded images marked on its out surface such that they are visible in images captured by the optical sensor arrangement 2. Each of these encoded images may uniquely encode a rotational position (or orientation) of the gear wheel 70. As such, the images may be printed or otherwise marked on the crests of the teeth or in the troughs between the teeth. The encoded images may take any suitable form, for example each may be a bar code or dot matrix.

Figure 6:
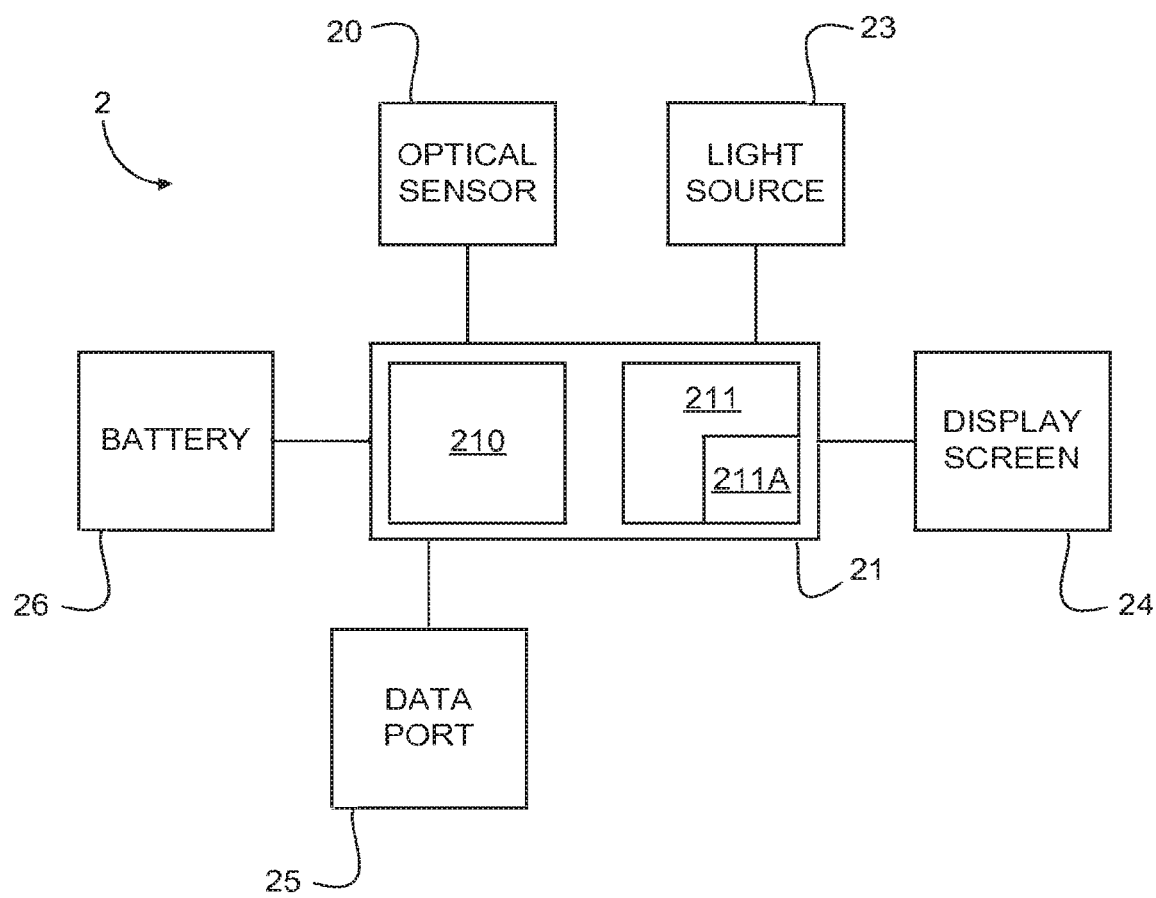
FIG. 6 is simplified block diagram of a sensor device according to embodiments of the disclosure.

FIG. 6 shows a simplified schematic block diagram of an optical sensor arrangement 2 according to various embodiments. The optical sensor arrangement 2 comprises an optical sensor 20, which may comprise an array of light sensitive elements. These are configured to output signals to circuitry 21. The circuitry 21 may be of any suitable composition and may comprise any combination of one or more processors and/or microprocessors 210 (for simplicity, hereafter referred to as "the at least one processor") suitable for causing the functionality described herein to be performed. The circuitry 21 may additionally or alternatively comprise any combination of one or more hardware-only components such as ASICs, FPGAs etc. (which are not shown in FIG. 6).

The circuitry 21 may further comprise any combination of one or more non-transitory computer readable memory media 211, such as one or both of ROM and RAM, which is coupled to the at least one processor 210. The memory 211 may have computer-readable instructions 211A stored thereon. The computer readable instructions 211A, when executed by the at least one processor 210 may cause the optical sensor arrangement 2 to perform the functionality described in this specification, such as controlling operation of the sensor 20 and interpreting the signals received therefrom.

The optical sensor arrangement 2 comprises at least one light source 23. The light source 23 is for illuminating the encoded information 66 on the number sleeve 15A and the encoded images on the gear wheel 70. The sensor 20 is configured read the encoded information by capturing an image. The image is captured by detecting the light reflected back from different parts of the surface(s) on which the image is provided. The captured images are then passed to the circuitry 21 for interpretation.

The optical sensor arrangement 2 may further comprise one or both of a display screen 24 (such as an LED or LCD screen) and a data port 25. The display screen 24 may be operable under the control of the circuitry 21 to display information regarding operation of the drug delivery device 1 to the user. For instance, the information determined by the optical sensor arrangement 2 may be displayed to the user. The information determined by the optical sensor arrangement 2 may include the current mode of operation of the device 1 and the delivered medicament dose.

The data port 25 may be used to transfer stored information relating to the operation of the drug delivery device 1 from the memory 211 to a remote device such a PC, tablet computer, or smartphone. Similarly, new software/firmware may be transferred to the sensor device via the data port 25. The data port 25 may be a physical port such as a USB port or may be a virtual, or wireless, port such as an IR, WiFi or Bluetooth transceiver. The optical sensor arrangement 2 may further comprise a removable or permanent (preferably rechargeable with e.g. photovoltaic cells) battery 26 for powering the other components of the device 2. Instead of the battery 26, a photovoltaic or capacitor power source may be used.

The optical sensor arrangement 2 may be configured to capture numerous images of the number sleeve 15A and gear wheel 70 and to determine from these whether the drug delivery device 1 is in a dialing mode or a delivery mode and if the device 1 is in a delivery mode, what dose of medicament has been delivered. As previously described, the gear wheel 70 has teeth which engage corresponding teeth on the drive sleeve 72. This engagement may occur at all times, or alternatively only when the drive sleeve 72 is shifted axially when the button 11 is depressed. In either case, as the drive sleeve 72 does not rotate during a dialing process, the gear wheel 70 also remains stationary during dialing. The optical sensor arrangement 2 may be configured to capture images at regular intervals whenever a dose is being dialed i.e. whenever it is detected that the number sleeve 15A is rotating. If it can be seen in any two images that the number sleeve 15A has moved, but that gear wheel 70 has remaining stationary, then it can be inferred that the device 1 is in a medicament dose dialing mode. If it can be seen in any two images that both the number sleeve 15A and the gear wheel 70 have moved, then it can be inferred that the device 1 is in a medicament dose delivery mode. The fact that the number sleeve 15A and gear wheel 70 rotate in opposite directions during the dose delivery process may make it easier for the optical sensor arrangement 2 to determine that only the number sleeve 15A is rotating in the dose dialing mode.

In order to determine a dose which has been delivered from the drug delivery device 1, the optical sensor arrangement 2 compares an image taken at the beginning of the dose dispensing process and at the end of the dose dispensing process. The position of the gear wheel 70 before and after the dispense process is compared with the position of the number sleeve 15A at the beginning of the dispense process (the number sleeve 15A always returns to the same position at the end of the dispense process provided that the whole dialed dose is ejected). In some embodiments, the number sleeve may occupy one of 24 unique rotational orientations, however up to 120 units of medicament may be dialed in and delivered from the device 1. The number sleeve 15A may therefore undergo more than one full revolution. If only the number sleeve were present, then it would not be possible for the optical sensor arrangement 2 to determine the absolute position of the number sleeve 15A. For example, it would not be possible to distinguish between a dialed dose of 24 units and 48 units, as the number sleeve 15A would be in the same rotational orientation in these cases. It would therefore not be possible to determine the dispensed dose with certainty.

Thus the gear wheel 70 is provided with a different number of teeth. In particular, the lowest common multiple of the number of teeth of the gear wheel and the number of unique rotational positions of the number sleeve 15A is greater than the maximum dose which can be dialed into the device 1. For example, the gear wheel 70 may comprise 7 teeth, the number sleeve 15A may have 24 unique positions per revolution and the maximum dialed dose may be 120 units. The lowest common multiple of 7 and 24 is 168. In another example, the number sleeve 15A may have only 20 unique rotational orientations. The maximum dialable dose may still be 120 units or may be reduced, for example to 100 units. In this case a gear wheel having 9 teeth, each with a unique encoded image, could be used. In general the number sleeve 15A may have an even number of unique rotational orientations and the gear wheel 70 may have an odd number of unique rotational orientations. However, in some embodiments the arrangement may be reversed such that the number sleeve 15A has an odd number of unique rotational orientations and the gear wheel 70 has an even number. Software residing in the optical sensor arrangement 2 is configured to isolate the two encoded images visible in each captured image, so that the positions of the number sleeve 15A and gear wheel 70 are accurately determined.

FIG. 7 is a table illustrating the way in which the optical sensor arrangement 2 can determine with certainty the medicament dose that has been delivered using the start and end orientations of the number sleeve 15A and gear wheel 70. For example, if 3 units are dialed in, then both the number sleeve 15A and gear wheel 70 will display the encoded image associated with the third tooth (the third unique rotational orientation for each component). If 27 units are dialed in, the number sleeve will again display the encoded image associated with the third tooth, however the gear wheel will display the encoded image associated with the sixth tooth. Thus the gear wheel 70 effectively allows the optical sensor arrangement 2 to determine how many complete rotations the number sleeve 15A has performed.

In order to reduce power consumption, the optical sensor arrangement 2 may not be powered on at all times, but may instead be "woken" in response to movement of the dose setting mechanism. Initial movement of the number sleeve 15A when a dialing process begins may trigger the wake up of the optical sensor arrangement 2. For example, if the optical sensor arrangement 2 is part of an attachable supplemental device, the supplemental device may be provided with a mechanical sensing pin which is caused to move when the number sleeve 15A moves from a zero dose position to a single unit dose position. If the optical sensor arrangement 2 is integral with the drug delivery device 1, then the sensing pin is internal or may be replaced with a conductive, magnetic, capacitive or optical sensor. The 'wake-up' signal may last until the drug delivery device 1 switches to a drug delivery mode, or until it is detected that the rotational components have been stationary for a predetermined period of time.

Alternatively, the optical sensor arrangement 2 may be configured to capture images only during the medicament dose dispensing process, or only and the beginning and end of the medicament dose dispensing process. Thus, the trigger may wake-up the optical sensor arrangement 2 when the button 11 is depressed.

The invention claimed is:

1. An optical decoding system comprising:
 a single optical sensor integral with or attachable to a housing of a drug delivery device and configured to:
  be directed at two or more movable components of a dose setting and dispensing mechanism of the drug delivery device,
  capture light reflected by the two or more movable components, and
  output electrical signals based on the captured light; and
 a processor configured to:
  cause the single optical sensor to capture light reflected by the two or more movable components, and
  receive the signals output by the single optical sensor.

2. The optical decoding system according to claim 1, wherein the signals output by the single optical sensor represent captured information associated with the two or more movable components.

3. The optical decoding system according to claim 1, wherein the processor is configured to cause the single optical sensor to capture the light reflected by the two or more movable components at least at a beginning and an end of a medicament dose dispensing process.

4. The optical decoding system according to claim 1, wherein the processor is configured to determine information relating to operation of the drug delivery device based on the signals output by the single optical sensor.

5. The optical decoding system according to claim 1, wherein the processor is configured to cause the single optical sensor to capture light reflected by the two or more movable components during a medicament dose setting process.

6. The optical decoding system according to claim 1, wherein the processor is configured to determine based on the signals output by the optical sensor whether the drug delivery device is in a medicament dose dialing mode or in a medicament dose dispensing mode.

7. The optical decoding system according to claim 6, wherein:
 in the medicament dose dialing mode, a first movable component of the two or more movable components is configured to move in a first direction and a second movable component of the two or more movable components remains stationary, and
 in the medicament dose dispensing mode the first movable component of the two or more movable components is configured to move in a second direction opposite to the first direction and the second movable component of the two or more movable components is configured to move in the first direction.

8. The optical decoding system according to claim 1, wherein the processor is configured to identify, from the signals output by the single optical sensor, encoded images associated with the two or more movable components, each encoded image encoding a different position of a respective movable component of the two of more movable components.

9. The optical decoding system according to claim 1, wherein a lowest common multiple of a number of unique positions of the two or more movable components is higher than a maximum dose which can be dialed into the drug delivery device.

10. The optical decoding system according to claim 1, wherein the processor is configured to:
determine positions of at least two of the two or more movable components at a beginning and an end of a medicament dose dispensing process based on the signals output by the single optical sensor, and
determine an amount of medicament dispensed based on the determined positions.

11. The optical decoding system according to claim 1, wherein a first movable component of the two or more movable components comprises a hollow cylindrical number sleeve having numbers marked on a first portion of an outer surface of the first movable component, and wherein encoded images are provided on a second portion of the outer surface.

12. The optical decoding system according to claim 1, wherein a second movable component of the two or more movable components comprises a gear wheel having a plurality of teeth.

13. The optical decoding system according to claim 12, wherein encoded images are marked on a crest of each of the plurality of teeth.

14. The optical decoding system according to claim 1, wherein the optical sensor is configured to be activated by movement of at least one of the two or more movable components.

15. The optical decoding system according to claim 1, wherein the optical decoding system comprises a switch, and wherein a change in a state of the switch is configured to cause the optical sensor to be activated.

16. The optical decoding system according to claim 15, wherein the drug delivery device and the switch are configured to be arranged such that the state of the switch changes when the drug delivery device moves from a zero unit drug dose arrangement to a single unit drug dose arrangement.

17. The optical decoding system according to claim 1, comprising a display device,
wherein the processor is configured to cause the display device to display an indication of an amount of medicament that has been delivered.

18. The optical decoding system according to claim 1, comprising one or more LEDs configured to illuminate portions of the at least one of the two or more movable components.

19. The optical decoding system according to claim 1, wherein the optical decoding system is part of a supplementary device configured to be attached to the drug delivery device.

20. The optical decoding system according to claim 1, wherein the optical decoding system comprises a switch configured to change between a first state and a second state upon movement of the at least one of the two or more movable components and wherein a change in state between the first state and the second state causes the optical sensor to be activated.

21. A medicament delivery system comprising:
a drug delivery device comprising two or more movable components, each movable component having a respective plurality of encoded images disposed around an outer surface of the movable component, wherein each of the encoded images corresponds to a discrete position of a respective one of the two or more movable components; and
an optical decoding system retained in a housing of the drug delivery device, the optical decoding system comprising:
a single optical sensor configured to:
be directed at the two or more movable components,
capture light reflected by the two or more movable components, and
output electrical signals based on the captured light, and
a processor configured to:
cause the single optical sensor to capture light reflected by the two or more movable components,
receive the signals output by the single optical sensor, and
determine a position of the two or more movable components based on the electrical signals output by the single optical sensor.

22. The medicament delivery system according to claim 21, wherein:
a first movable component of the two or more movable components comprises a hollow cylindrical number sleeve having numbers marked on a first portion of an outer surface of the first movable component,
encoded images on the number sleeve are provided on a second potion of the outer surface of the first movable component,
a second movable component of the two or more movable components comprising a gear wheel having a plurality of teeth, and
the gear wheel is configured to be engaged with a drive sleeve of the drug delivery device during a medicament dose dispensing process.

* * * * *

UNITED STATES PATENT AND TRADEMARK OFFICE
CERTIFICATE OF CORRECTION

PATENT NO. : 11,213,629 B2  Page 1 of 1
APPLICATION NO. : 16/993913
DATED : January 4, 2022
INVENTOR(S) : Markus Ploch It is certified that error appears in the above-identified patent and that said Letters Patent is hereby corrected as shown below:

In the Claims

Column 11, Line 10, Claim 8, delete "two of" and insert -- two or --

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*